United States Patent [19]
Peterson et al.

[11] Patent Number: 5,345,933
[45] Date of Patent: Sep. 13, 1994

[54] IMPLANTABLE MEDICAL DEVICE WITH A PROTECTED MEDICATION LAYER

[75] Inventors: Lars-Olof Peterson, Bromma; Ulf Lindegren, Enskede, both of Sweden; Brigitte Stroetmann, Uttenreuth, Fed. Rep. of Germany

[73] Assignee: Siemens Aktiengesellschaft, Munich, Fed. Rep. of Germany

[21] Appl. No.: 944,265

[22] Filed: Sep. 14, 1992

[30] Foreign Application Priority Data

Sep. 25, 1991 [SE] Sweden ............................ 91027789

[51] Int. Cl.$^5$ ............................................. A61B 5/04
[52] U.S. Cl. ................................... 128/639; 604/20
[58] Field of Search ............... 128/639, 640, 641, 644, 128/785, 785, 786; 604/20

[56] References Cited

U.S. PATENT DOCUMENTS

| | | | |
|---|---|---|---|
| 4,281,668 | 8/1981 | Richter et al. | 128/784 |
| 4,281,669 | 8/1981 | MacGregor | 128/784 |
| 4,304,591 | 12/1981 | Mueller et al. | 71/93 |
| 4,336,811 | 6/1982 | Beck et al. | 128/784 |
| 4,577,642 | 3/1986 | Stokes | 128/784 |
| 4,682,602 | 7/1987 | Prohaska | 128/784 |
| 4,711,251 | 12/1987 | Stokes | 128/784 |
| 4,722,726 | 2/1988 | Sanderson et al. | 604/20 |
| 4,784,161 | 11/1988 | Skalsky et al. | 128/785 |
| 5,087,243 | 2/1992 | Avitall | 604/20 |
| 5,103,837 | 4/1992 | Weidlich et al. | 128/784 |
| 5,135,480 | 8/1992 | Bannon et al. | 128/639 |
| 5,169,383 | 12/1992 | Gyory et al. | 604/20 |

FOREIGN PATENT DOCUMENTS

WO86/00795  2/1986  PCT Int'l Appl. .

*Primary Examiner*—Jerome L. Kruter
*Attorney, Agent, or Firm*—Hill, Steadman & Simpson

[57] ABSTRACT

An implantable medical device has surfaces that are in communication with the tissue of the patient after an implantation. At least one part of these surfaces is provided with at least one layer composed of a medication. In order to simply and reliably control the administration of a desired quantity of the medication, the medication layer is covered by at least one layer composed of an ion exchanger material.

13 Claims, 1 Drawing Sheet

IMPLANTABLE MEDICAL DEVICE WITH A PROTECTED MEDICATION LAYER

BACKGROUND OF THE INVENTION

1. Field of the Invention

The present invention is directed to an implantable medical device having surfaces that are in communication with the tissue of a patient after an implantation, with at least a part of these surfaces provided with at least one layer composed of a medication.

2. Description of the Prior Art

A heart pacemaker electrode is disclosed in U.S. Pat. No. 4,711,251 having a medication layer on its electrode head that has an inflammation-inhibiting effect when the electrode head presses against the heart wall. The growth of fibrous tissue in the region of the electrode head can be avoided or reduced in this way. The disadvantage of the medication layer is that it comes into contact with body fluids during the implantation procedure and is thus at least partially dissolved before the electrode head reaches its ultimate position at the heart wall.

U.S. Pat. No. 4,304,591 discloses a hydrophilic polymer layer that is employed in implantations and serves as carrier for, among other things, medications. In this known arrangement as well, the medication can undesirably separate from the polymer layer when it comes into contact with body fluid.

A heart pacemaker electrode is disclosed in European Application No. 0 388 480 having an electrode head provided with a layer composed of a hydrophilic polymer in which an inflammation-inhibiting steroid is embedded. Although the embedded medication is in fact prevented from prematurely dissolving in this way, the release of this steroid is difficult to control. Moreover, the quantity of medication that can be embedded in the layer is generally too small. When relatively large quantities of a medication are required, the polymer layer must be made so thick that the electrode head can no longer be kept small.

SUMMARY OF THE INVENTION

An object of the present invention is to provide an implantable medical device having a layer of medication on a surface thereof, wherein the administration of a desired quantity of the medication can be simply and reliably controlled.

This object is achieved in accordance with the principles of the present invention in an implantable medical device wherein the medication layer is covered by at least one layer composed of an ion exchanger material. The ion exchanger material layer serves not only as protection for the medication layer during an implantation, but also allows the medication to pass therethrough so as to be administered in a predetermined way, dependent on the thickness of the ion exchanger material layer.

The implantable medical device may be a heart stimulation device or a part thereof. A heart stimulation device is, for example, a heart pacemaker or a defibrillation device.

The implantable device may also be a heart stimulation electrode, i.e. any type of heart pacemaker or defibrillation electrode.

In a preferred embodiment of the invention the heart stimulation electrode is a heart pacemaker electrode having at least one stimulation surface, wherein only the stimulation surface is provided with at least one medication layer that is covered by at least one ion exchanger material layer. It is of particular significance given these small stimulation surfaces, that a defined quantity of medication diffuses through the ion exchanger material layer given an implanted electrode in order thus to prevent fibrous tissue from being formed in the region of this stimulation surface.

Preferably the stimulation surface is formed of microporous material. Such a material can be carbon or titanium nitride having a microporous structure. It is thus possible to obtain an extremely small electrode head.

The invention can be advantageously employed in combination with a heart pacemaker electrode having an electrode head comprising a surface area of a maximum of 4 mm$^2$. An adequate quantity of medication and a covering layer of ion exchanger material can be applied to the electrode head and supplied to the heart wall in order to prevent inflammations in the region of the head given such an extremely small surface without significantly enlarging the electrode head.

In a further embodiment of the invention, medication layers and ion exchanger material layers are applied to the surface alternating in a plurality of layers. A longer-lasting administration of medications to the tissue of a patient can thus be achieved. Moreover, medications of different types can be applied between the ion exchanger material layers.

In another embodiment of the invention, the thickness of the ion exchanger material layer and the thickness of the medication layer can be varied independently of one another. The control of the administration of the quantity of medication can thereby be refined.

DESCRIPTION OF THE PREFERRED EMBODIMENTS

Figure 1:
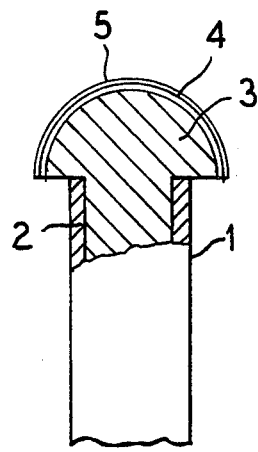
FIG. 1 is a side view, partly in section, of the head of a pacemaker electrode constructed in accordance with the principles of the present invention, in a first embodiment having a single layer of medication and a single layer of ion exchanger material.

The distal end of a heart pacemaker electrode 1 is shown in FIG. 1, partially in cross section. The electrode 1 has an insulation 2 and an electrode head 3 which transmits stimulation pulses to the heart of a patient. The stimulation surface of the electrode head 3, which is formed of a microporous material, is provided with a layer 4 of a medication that is covered by a layer 5 composed of a hydrophilic ion exchanger material. The ion exchanger material layer 5 serves as protection for the medication layer 4 when storing the electrode and during the implantation phase. Examples of ion exchange materials are Nafion, Termeon and Carboxylic acid resin. When the heart pacemaker electrode 1 is applied against the heart wall, the medication diffuses through the ion exchanger material, reaches the heart wall and prevents a potential tissue reaction that otherwise frequently leads to an inflammation of the tissue in the region of the electrode head. The thicknesses of the medication and ion exchanger material layers 4 and 5 are between 0.5 $\mu$m and 4 $\mu$m, preferably 2 $\mu$m. The thicknesses of the layers 4 and 5 can also be varied independently of one another. By covering the medication layer or layers with a single ion exchanger material layer, the medication diffuses quickly through the ion exchanger material layer 5 in the desired way. When a plurality of ion exchanger material layers are applied, the passage of the medication ensues more slowly. It is thus possible to define the administration rate of the medication with the thickness of the ion exchanger material layer. A relatively large quantity of medications can be stored on the electrode head 3 by applying a plurality of medication layers on the stimulation surface of the electrode 1.

Figure 2:
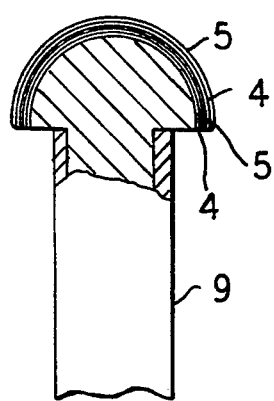
FIG. 2 is a side view, partly in section, of the head of a pacemaker electrode constructed in accordance with the principles of the present invention, and a second embodiment having multiple, alternating layers of medication and ion exchanger material.

FIG. 2 shows a heart pacemaker electrode 9 that is similar to the electrode 1 shown in FIG. 1. In FIG. 2 the medication layer 4 and the ion exchanger material layer 5 are applied to the stimulation surface in alternation in a plurality of layers. A longer-lasting administration of medication is obtained as a result of this structure. It is also possible to employ different types of medication between the ion exchanger material layers which could otherwise be difficult to dose given a mixture of the medication types.

Figure 3:
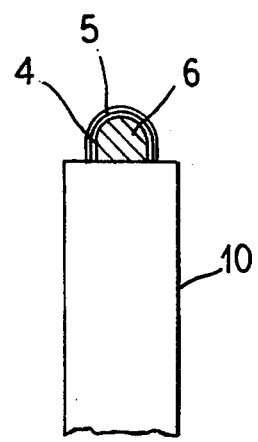
FIG. 3 is a side view, partly in section, of a further embodiment of a pacemaker electrode head constructed in accordance with the principles of the present invention.

FIG. 3 shows a heart pacemaker electrode 10 having an electrode head 6 whose surface is a maximum of 4 mm$^2$. Even such a small electrode head can store a relatively great quantity of medications with the assistance of the ion exchanger material layer 5 that covers a medication layer 4, this medication being capable of being administered at the application point of the electrode head. The head has thereby remained small despite the applied layers 4 and 5.

Figure 4:
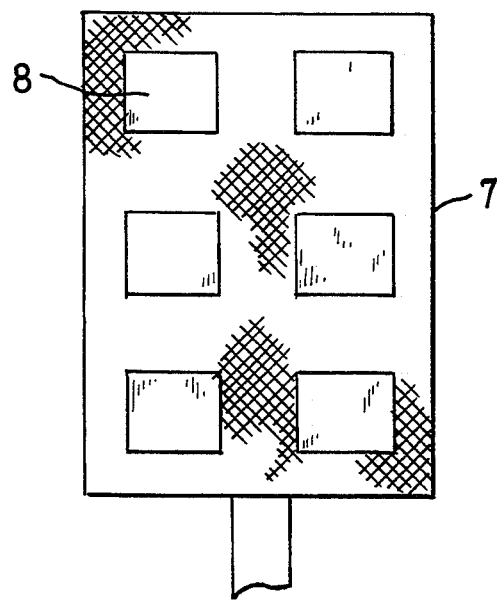
FIG. 4 is plan view of a defibrillator patch electrode, constructed in accordance with the principles of the present invention.

FIG. 4 shows a defibrillation electrode of the so-called patch type having a carrier 7 with a plurality of exposed electrode regions 8 that transmit the stimulation pulses to the heart. Given such a defibrillation electrode, the surfaces of the electrode regions 8, the entire side or both sides of the patch electrode can be provided with a medication layer that is covered with an ion exchanger material layer. An endocardial defibrillation electrode (not shown) can also be provided with such layers.

The housing of a heart pacemaker or defibrillation device or the housing of an infusion pump can also be entirely or partially provided with the medication and ion exchanger material layers in the way set forth herein.

Although modifications and changes may be suggested by those skilled in the art, it is the intention of the inventors to embody with the patent warranted hereon all changes as reasonably and properly come within the scope of their contribution to the art.

We claim as our invention:

1. An implantable medical device having ion exchange properties, said device having surfaces which are in communication with the tissue of a patient after implantation of said device, at least a part of these surfaces being covered by a layer composed of a medication, and said layer composed of a medication being covered by at least one layer composed of an ion exchanger material.

2. An implantable medical device as claimed in claim 1 wherein said device is a heart simulation device or a part thereof.

3. An implantable medical device as claimed in claim 1 wherein said device is a heart stimulation electrode.

4. An implantable medical device as claimed in claim 3 wherein said heart stimulation electrode is a heart pacemaker electrode having at least one stimulation surface, said stimulation surface being covered by said at least one medication layer and said at least ion exchanger material layer.

5. An implantable medical device as claimed in claim 4 wherein said stimulation surface consist of a microporous material.

6. An implantable medical device as claimed in claim 4 wherein said stimulation surface of said heart pacemaker electrode has a maximum area of 4 mm$^2$.

7. An implantable medical device as claimed in claim 1 wherein said device is an infusion pump.

8. An implantable medical device as claimed in claim 1 comprising a plurality of said layers of medication and a plurality of said layers of ion exchanger material, disposed in alternation above one another.

9. An implantable medical device as claimed in claim 1 wherein said layer of medication has a thickness in a range between 0.5 $\mu$m and 4 $\mu$m.

10. An implantable medical device as claimed in claim 9 wherein said layer of medication has a thickness of approximately 2 $\mu$m.

11. An implantable medical device as claimed in claim 1 wherein said layer of ion exchanger material has a thickness in a range between 0.5 $\mu$m and 4 $\mu$m.

12. An implantable medical device as claimed in claim 1 wherein said layer of ion exchanger material has a thickness of approximately 2 $\mu$m.

13. An implantable medical device as claimed in claim 1 wherein each of said layer of medication and said layer of ion exchanger material have respective thicknesses which are independently variable.

* * * * *